United States Patent
Ylostalo et al.

(10) Patent No.: US 8,825,128 B2
(45) Date of Patent: Sep. 2, 2014

(54) SENSOR FOR MEASURING BIOSIGNALS

(75) Inventors: Antti Kustaa Antipas Ylostalo, Helsinki (FI); Magnus Johannes Kall, Helsinki (FI); Outi Kristiina Savinen, Helsinki (FI)

(73) Assignee: General Electric Company, Schenectady, NY (US)

( * ) Notice: Subject to any disclaimer, the term of this patent is extended or adjusted under 35 U.S.C. 154(b) by 204 days.

(21) Appl. No.: 13/213,500

(22) Filed: Aug. 19, 2011

(65) Prior Publication Data
US 2012/0053439 A1 Mar. 1, 2012

(30) Foreign Application Priority Data

Aug. 27, 2010 (EP) .................................... 10174246

(51) Int. Cl.
 *A61B 5/0408* (2006.01)
 *A61B 5/0478* (2006.01)
 *A61B 5/0488* (2006.01)
 *A61B 5/0492* (2006.01)

(52) U.S. Cl.
 CPC ............. *A61B 5/0408* (2013.01); *A61B 5/0492* (2013.01); *A61B 2562/125* (2013.01); *A61B 5/0478* (2013.01)
 USPC ........... 600/372; 600/391; 600/393; 600/396; 600/397

(58) Field of Classification Search
 USPC ........................ 600/372, 391–393, 396, 397
 See application file for complete search history.

(56) References Cited

U.S. PATENT DOCUMENTS

| | | | | |
|---|---|---|---|---|
| 3,977,392 | A | * | 8/1976 | Manley .......................... 600/392 |
| 4,362,165 | A | | 12/1982 | Carmon et al. |
| 4,370,984 | A | | 2/1983 | Cartmell |
| 4,516,581 | A | | 5/1985 | Sessions |
| 4,522,211 | A | | 6/1985 | Bare et al. |
| 4,570,637 | A | | 2/1986 | Gomes et al. |
| 4,736,752 | A | | 4/1988 | Munck et al. |
| 4,852,571 | A | | 8/1989 | Gadsby et al. |
| 4,934,383 | A | * | 6/1990 | Glumac .......................... 607/152 |
| 5,337,748 | A | * | 8/1994 | McAdams et al. ............. 600/396 |

(Continued)

FOREIGN PATENT DOCUMENTS

| | | |
|---|---|---|
| CN | 1852634 A | 10/2006 |
| CN | 101312688 A | 11/2008 |
| CN | 101658418 A | 3/2010 |

OTHER PUBLICATIONS

EP Search Report issued in connection with EP Application 10174246 on Dec. 1, 2010.

(Continued)

*Primary Examiner* — Lee S Cohen
(74) *Attorney, Agent, or Firm* — Global Patent Operation; Marc A. Vivenzio

(57) ABSTRACT

A sensor for measuring biosignals is provided. The sensor comprises at least one electrode comprising: a substrate comprising a flexible non-conductive material; a conductive layer configured to transfer electrical signals; a gel layer configured to transfer electrical signals; and a barrier layer configured to protect the conductive layer and transfer electrical signals, wherein the barrier layer deposited on the substrate, the gel layer is deposited on the barrier layer so that the gel layer covers only a part of the barrier layer, and the conductive layer is deposited over an area of the barrier layer which is outside of an area of the barrier layer on which the gel layer is deposited.

20 Claims, 1 Drawing Sheet

(56) References Cited

U.S. PATENT DOCUMENTS

| | | |
|---|---|---|
| 5,352,315 A | 10/1994 | Carrier et al. |
| 5,402,780 A * | 4/1995 | Faasse, Jr. .................. 600/392 |
| 5,406,945 A | 4/1995 | Riazzi et al. |
| 5,427,096 A | 6/1995 | Bogusiewicz et al. |
| 5,465,715 A | 11/1995 | Lyons |
| 5,565,143 A | 10/1996 | Chan |
| 5,566,672 A | 10/1996 | Faasse, Jr. |
| 5,622,168 A | 4/1997 | Keusch et al. |
| 5,707,502 A | 1/1998 | McCaffrey et al. |
| 5,785,040 A | 7/1998 | Axelgaard |
| 5,855,820 A | 1/1999 | Chan et al. |
| 6,434,410 B1 | 8/2002 | Cordero et al. |
| 8,126,530 B2 * | 2/2012 | Bare et al. .................. 600/397 |
| 2008/0287767 A1 | 11/2008 | Pasveer et al. |
| 2009/0043185 A1 * | 2/2009 | McAdams et al. ............ 600/372 |
| 2010/0041962 A1 | 2/2010 | Causevic et al. |
| 2010/0081913 A1 | 4/2010 | Cross et al. |
| 2010/0198044 A1 | 8/2010 | Gehman et al. |

OTHER PUBLICATIONS

Unofficial translation of Chinese Search Report from CN Patent Application No. 201110257763.0 dated Apr. 24, 2014.

* cited by examiner

SENSOR FOR MEASURING BIOSIGNALS

BACKGROUND OF THE INVENTION

1. Field of the Invention

The disclosure relates generally to a sensor for measuring biosignals such as Entropy, EEG, EKG, EMG; and more specifically to sensors which comprise at least one electrode comprising a substrate of flexible nonconductive material, a conductive layer, a gel layer and a barrier layer.

2. Description of Related Art

Electrodes which are used to record biosignals from the recording surface, for example the skin, generally require the use of a conductive liquid or solid gel to provide a continuous conductive path between the recording surface and the electrode sensing element. Conductive gels contain a salt, KCl or NaCl, in order to achieve electrical current flow. The preferred gel is one with a high salt content, since such a gel produces a better conductor than that obtained when using a gel with low salt content. In addition, the use of a high salt content typically requires less skin abrasion at the time of application to reduce the impedance of the skin-electrode interface after subsequent electrode application.

Biosignal measurement electrodes can be single electrodes or electrode arrays containing multiple electrodes at the same substrate. Electrodes typically contain an adhesive foam material that is used for attaching the electrode to living tissue, for example, a human forehead or chest depending on the use area. Electrode contains electrolyte gel with salt content that is in direct contact with tissue to enable measurement of the electrical signal. The typical use time of an electrode is dependent on the application and varies from minutes to several days.

Biosignal measurement sensor electrodes with high salt content traditionally have a 12 month shelf life. This is caused by many factors, for example, drying of the gel in the electrodes, but mainly by the changes that take place in the conductive layer and the barrier layer. The conductive layer can be, for example, silver (Ag) and the barrier layer can be, for example, silver/silver-chloride (Ag/AgCl). The layers are placed contiguously on top (tissue side) of each other. The changes are caused by the chemical reactions between the layers and electrolyte gels that have high salt content to maximize the signal quality and low impedance.

Traditionally as shown in FIG. 1 the barrier layer 3, for example, Silver/Silver Chloride (Ag/AgCl) is placed directly on the top (tissue side) of the conductive layer 2, for example, Silver (Ag). The gel 5 is placed directly on the top (tissue side) of the thin layer such as Ag/AgCl that acts as a barrier layer 3 between the conductive layer 2 such as Ag and the gel 5. This barrier layer 3 is very thin, usually from a few to tens of micrometers, and the gel 5 changes the features of the layer over time. If the gel contacts the Ag layer directly after a period of time, the performance of the Ag layer and the whole electrode deteriorates.

Another method known in the field to create a barrier layer is to add an active gel on the plain top surface (tissue side) of the conductive Ag layer. The gel modifies the Ag layer and chemically changes the top surface (tissue side) to Silver Chloride Ag/AgCl. The chemical reaction is controlled by adding a controlled amount of a substance to the plain silver that stops the chemical reaction at a defined point. However, this method creates a really thin AgCl layer on top (tissue side) of the Ag layer where the gel penetrating through the thin AgCl layer to Ag layer can lower the shelf life of the electrode.

The basic methods to manufacture such electrodes are well known in the field. These methods are used widely for manufacturing printed electronics. These methods are for example silk-screen printing, flexography, gravure, offset lithography and inkjet. All of these methods use printable inks such as silver (Ag) and silver/silver chloride (Ag/AgCl) that can be deposited on the flexible substrate in automated process enabling mass production of described sensors. A person who is skilled in the art can find various other techniques that can be used for manufacturing described electrode embodiment.

The disclosure provides a sensor for measuring biosignals that can avoid the limitations of the prior art.

BRIEF SUMMARY OF THE INVENTION

The shortcomings, disadvantages and problems of the electrode are addressed herein which will be understood by reading and understanding the following specification.

In an embodiment, a sensor is provided for measuring biosignals. The sensor comprises at least one electrode comprising: a substrate comprising a flexible non-conductive material; a conductive layer configured to transfer electrical signals; a gel layer configured to transfer electrical signals; and a barrier layer configured to protect the conductive layer and transfer electrical signals, wherein the barrier layer deposited on the substrate, the gel layer is deposited on the barrier layer so that the gel layer covers only a part of the barrier layer, and the conductive layer is deposited over an area of the barrier layer which is outside of an area of the barrier layer on which the gel layer is deposited.

In another embodiment, a sensor for measuring biosignals is provided. The sensor comprises at least one electrode comprising: a substrate comprising a flexible non-conductive material; a conductive layer configured to transfer electrical signals; a gel layer configured to transfer electrical signals; a barrier layer configured to protect the conductive layer and transfer electrical signals; and a foam element comprising a nonconductive material, wherein the barrier layer deposited on the substrate, the gel layer is deposited on the barrier layer so that the gel layer covers only a part of the barrier layer, and the conductive layer is deposited over an area of the barrier layer which is outside of an area of the barrier layer on which the gel layer is deposited, the foam element is arranged on top of the conductive layer, and the foam element is configured to restrict the area of the barrier layer on which the gel layer is deposited and form a barrier between the conductive layer and the gel layer.

Another embodiment relates to a method of making a sensor for measuring biosignals, the sensor comprising at least one electrode. The method comprises: providing a substrate of flexible non-conductive material; depositing a barrier layer on the substrate, the barrier layer configured to protect the conductive layer and transfer electrical signals; depositing a conductive layer on only a part of the barrier layer, the conductive layer configured to transfer electrical signals; and depositing a gel layer on only a part of the barrier layer that is inside of the part of the barrier layer on which the conductive layer has been deposited, the gel layer configured to transfer electrical signals.

Various other features, objects, and advantages of the invention will be made apparent to those skilled in the art from the accompanying drawings and detailed description thereof.

DETAILED DESCRIPTION OF THE INVENTION

Figure 2:
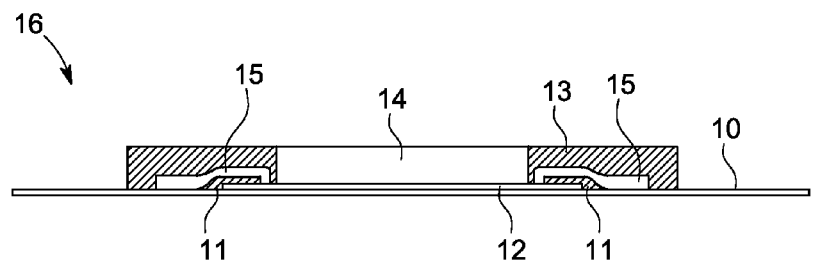
FIG. 2 is a schematical side view of an embodiment of an electrode for measuring biosignals.

FIG. 2 shows schematically an embodiment of an electrode for measuring biosignals. Reference number 10 shows a substrate of flexible nonconductive material. Reference number 11 shows a conductive layer for transferring electrical signals, especially from the electrode to a connector and further to a measuring device, but can also be used for transferring electrical signals from measuring device or the connector to the electrode. The conductive layer 11 can be made, for example, of silver (Ag) ink material. Reference number 14 shows a gel layer for transferring electrical signals, especially from a tissue to the electrode, but can be also used for transferring electrical signals from the electrode to the tissue. The gel layer 5 may have a predetermined salt content. Reference number 12 shows a barrier layer for protecting the conductive layer 11 from the chemical changes the gel can cause and thereby decreasing the shelf life and performance of the electrode. The barrier layer 12 is able to transfer electrical signals from gel layer 14 to conductive layer 11 and vice versa and also is able to prevent direct contact between the gel layer 14 and the conductive layer 11. To transfer electrical signals the barrier layer should be of a conductive material. The barrier layer 12 can be made, for example, of silver/silver chloride (Ag/AgCl) material. Reference number 13 shows a foam element of nonconductive material. Reference number 16 shows the whole electrode.

The electrode shown in FIG. 2 is a schematical view. A person skilled in the art immediately understands that the structure described also comprise appropriate accessories such as connectors, etc.

Figure 3:
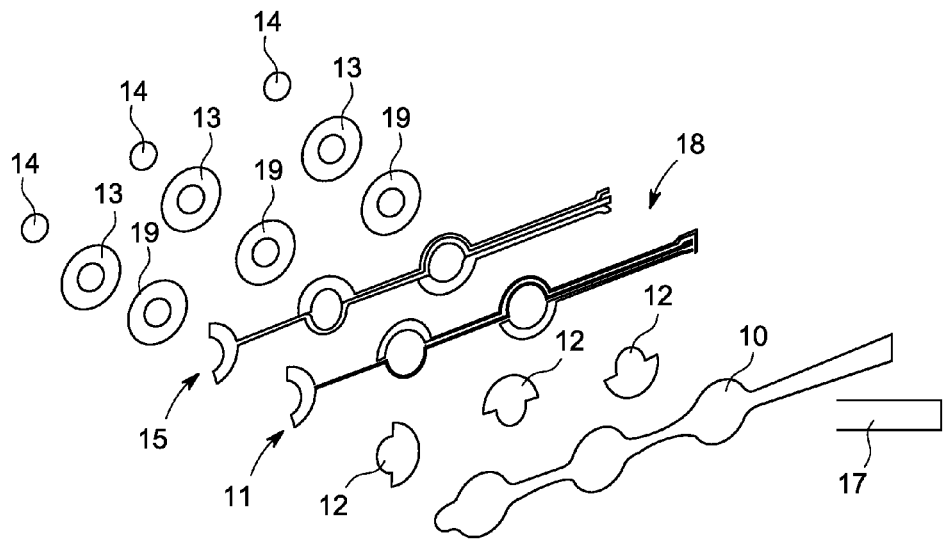
FIG. 3 is an exploded perspective view of the embodiment shown in FIG. 2.

FIGS. 2 and 3 describe an embodiment of the electrode for measuring biosignals. FIG. 3 describes corresponding details with the same reference numbers as FIG. 2. FIG. 2 shows the basic structure of the electrode and FIG. 3 shows a version of the embodiment using three electrodes described in FIG. 2 in a sensor. In the embodiment of FIG. 3 the electrodes are connected together with a flexible non-conductive substrate 10, FIGS. 2 and 3 must not however be understood restrictively, i.e. the number of the assemblies used can be varied quite freely according to the existing need.

In the embodiment of FIGS. 2 and 3, the barrier layer 12 is deposited, such as printed directly, on the substrate 10. The barrier layer 12 can either be silver/silver chloride ink or silver ink, which is chemically modified with an active gel to have a top (tissue side) surface of AgCl as described earlier. The conductive layer 11 is deposited over to contact the area of the barrier layer 12 which is outside of the area of the barrier layer contacting with the gel layer 14. The gel layer 14 is placed on the barrier layer so that the gel layer covers only a part of the barrier layer 12.

The term "top side" refers the side facing in use to the tissue for example human skin, when the sensor is attached to the skin.

In the embodiments of FIGS. 2 and 3 the foam element 13 is formed as a ring element, and the shapes of the conductive layer 11 and the other layers are formed to conform to the shape of the foam element 13. Here again it must be understood that the form shown must not be understood restrictively but the forms used can be varied freely according to the existing need.

FIG. 3 shows also with a reference number 17 a connector which can be attached to the structure. The connector can be attached to the structure in the manufacturing stage of the electrode or alternatively said connector can be attached later. In FIG. 3 reference number 18 shows the whole sensor comprising three electrodes 16 shown in FIG. 2.

In the embodiment of FIGS. 2 and 3 the area of the barrier layer 12 contacting with the gel layer 14 is restricted by the foam element 13 made of nonconductive material arranged on top side of the conductive layer. In the embodiment of FIGS. 2 and 3 the foam element 13 made of nonconductive material thus forms a barrier element between the conductive layer 11 and the gel layer 14. Gel material in the gel layer 14 can be liquid gel (wet gel) or solid gel. If wet gel is used then a sponge element (not shown in the figures) may be also used, in that case the sponge element may be impregnated by the wet gel. The foam element 13 can be attached to the electrode or its substrate by using an appropriate adhesive layer 19 shown in FIG. 3. In another embodiment the adhesive layer can be used to attach the electrode directly to living tissue such as human skin. The adhesive layer can also be used as a mechanical barrier layer preventing the gel layer to contact the conductive layer.

Figure 1:
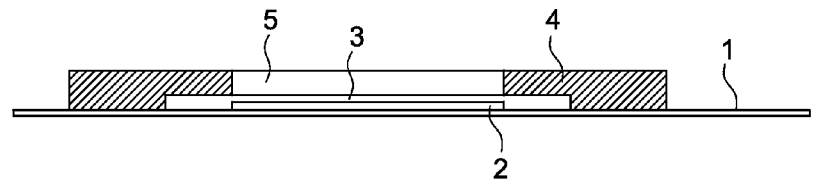
FIG. 1 is a schematical side view of a typical prior art electrode for measuring biosignals.

In the embodiment of FIGS. 2 and 3 the conductive layer (Ag layer) 11 and barrier layer (Ag/AgCl layer or Ag layer modified with active gel to contain top (tissue side) surface of AgCl) 12 are placed on the substrate 10 in opposite order when compared to the structure of FIG. 1, i.e. the conductive layer 11 is placed on top of the barrier layer 12 so that the whole conductive layer 11 is placed outside the area of the electrode gel layer 14. The conductive layer 11 contacts only the outer edge of the barrier layer 12 without a contact on conductive layer Ag material covered with the electrolyte gel material of the gel layer.

FIG. 1 shows a typical prior art electrode construction, for example, wherein the foam element 4 that is used to adhere the electrode to the patient is not used as a barrier.

In the embodiment of FIGS. 2 and 3 the foam element 13 is placed on top of the conductive layer 11 and it acts as a barrier layer between conductive layer 11 and gel layer 14.

Also when using flexible circuit manufacturing processes it is common that a protective layer 15 made of nonconductive material is placed on top (tissue side) of the conductive layer 11 to protect the conductive layer. The protective material can be made for example of dielectric material. This protective layer may also act as a barrier element between the conductive layer and the gel layer.

FIGS. 2 and 3 show embodiments without direct contact between the silver material of the conductive layer 11 and the electrolyte gel material of the gel layer 14. This enables a longer physical distance and a better barrier between the high salt content electrolyte gel and the contact layer when compared to the structures used in the prior art. This leads to improved shelf life of the electrodes.

On the embodiment shown in FIGS. 2 and 3 the contact area between the conductive layer 11 and the barrier layer 12 (Ag/AgCl layer or Ag layer modified with active gel to contain top (tissue side) surface of Ag/AgCl) can be formed to have at least equal performance when compared to the structures used in the prior art. Based on the initial testing with the embodiment of FIGS. 2 and 3 one can achieve improved shelf life and at least equal performance (measuring characteristics), for the electrode as achieved with the structures used in the prior art.

Based on the initial testing for the described embodiment, 18 months shelf life is easy to achieve with the high salt content electrode and according to further testing it is very likely that at least 24 months up to 36 months of shelf life is possible. Based on the initial testing the increased shelf life also improves the reliability and stability of the measurement characteristics over time compared to the structures used in the prior art.

This written description uses examples to disclose the embodiments of the invention, including the best mode, and also to enable any person skilled in the art to practice the embodiments of the invention, including making use of any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A sensor for measuring biosignals, the sensor comprising at least one electrode comprising:
    a substrate comprising a flexible non-conductive material;
    a conductive layer configured to transfer electrical signals;
    a gel layer configured to transfer electrical signals;
    a foam element; and
    a barrier layer configured to protect the conductive layer and transfer electrical signals,
    wherein:
        a portion of the conductive layer is deposited on a first area of a surface of the barrier layer,
        the barrier layer is deposited on the substrate so that a portion of the barrier layer in contact with the conductive layer is positioned between the substrate and the conductive layer,
        the gel layer is deposited on a second area of the surface of the barrier layer so that the gel layer covers only a part of the barrier layer, and
        a portion of the foam element is deposited on a third area of the surface of the barrier layer, wherein the third area is between the first area and the second area.

2. The sensor of claim 1, wherein the gel layer is deposited on only a part of the barrier layer which is not covered by the conductive layer.

3. The sensor of claim 1, wherein the barrier layer is configured to transfer electrical signals from the gel layer to the conductive layer and/or from the conductive layer to the gel layer and is configured to prevent direct contact between the gel layer and the conductive layer.

4. The sensor of claim 1, wherein the barrier layer is contiguous with the conductive layer.

5. The sensor of claim 1, wherein the at least one electrode further comprises a protective layer made of nonconductive material arranged on top of the conductive layer and is configured as a barrier element.

6. The sensor of claim 5 wherein the protective layer comprises a dielectric layer configured as a barrier element.

7. The sensor of claim 1, wherein the foam element is configured as a barrier element.

8. The sensor of claim 1, wherein the conductive layer comprises a silver ink material.

9. The sensor of claim 1, wherein the barrier layer comprises a silver chloride layer or a silver layer modified with an active gel to provide a top surface of silver chloride.

10. The sensor of claim 1, wherein the sensor further comprises more than one electrode, wherein each electrode is connected to each other by the substrate.

11. A sensor for measuring biosignals, the sensor comprising at least one electrode comprising:
    a substrate comprising a flexible non-conductive material;
    a conductive layer configured to transfer electrical signals;
    a gel layer configured to transfer electrical signals;
    a barrier layer configured to protect the conductive layer and transfer electrical signals; and
    a foam element comprising a nonconductive material,
    wherein:
        a portion of the conductive layer is deposited on a first area of a surface of the barrier layer,
        the barrier layer is deposited on the substrate so that a portion of the barrier layer in contact with the conductive layer is positioned between the substrate and the conductive layer,
        the gel layer is deposited on a second area of the surface of the barrier layer so that the gel layer covers only a part of the barrier layer,
        the foam element is arranged on top of the conductive layer, wherein a portion of the foam element is deposited on a third area of the surface of the barrier layer, wherein the third area is between the first area and the second area so that the foam element restricts the second area of the surface of the barrier layer on which the gel layer is deposited and forms a barrier between the conductive layer and the gel layer.

12. The sensor of claim 11, wherein the electrode further comprises a nonconductive layer placed between the foam element and the conductive layer, wherein the nonconductive layer is configured as a barrier element.

13. The sensor of claim 12, wherein the nonconductive layer placed between the foam element and the conductive layer is a dielectric layer configured as a barrier element.

14. The sensor of claim 11, wherein the conductive layer comprises a silver ink material.

15. The sensor of claim 11, wherein the barrier layer comprises a silver chloride layer or a silver layer that is modified with active gel to provide a top surface of silver chloride.

16. The sensor of claim 11, wherein the sensor further comprises more than one electrode, wherein each electrode is connected to each other by the substrate.

17. A method of making a sensor for measuring biosignals, the sensor comprising at least one electrode, the method comprising:
    providing a substrate of flexible non-conductive material;
    depositing a barrier layer on the substrate;
    depositing a portion of a conductive layer on a first area of a surface of the barrier layer, wherein a portion of the barrier layer is positioned between the substrate and the conductive layer;
    depositing a gel layer on a second area of the surface of the barrier layer; and
    depositing a portion of a foam element on a third area of the surface of the barrier layer, wherein the third area is between the first area and the second area,
    wherein the barrier layer is configured to protect the conductive layer, and the barrier layer, the conductive layer and the gel layer are configured to transfer electrical signals.

18. The method of claim 17, wherein the method further comprises depositing a protective layer comprising a nonconductive material on top of the conductive layer, wherein the protective layer is configured as a barrier element.

19. The method of claim 18, wherein the protective layer comprises a dielectric layer configured as a barrier element.

20. The method of claim 17, wherein the foam element is configured as a barrier element.

* * * * *

UNITED STATES PATENT AND TRADEMARK OFFICE
CERTIFICATE OF CORRECTION

| | | |
|---|---|---|
| PATENT NO. | : 8,825,128 B2 | Page 1 of 1 |
| APPLICATION NO. | : 13/213500 | |
| DATED | : September 2, 2014 | |
| INVENTOR(S) | : Ylostalo et al. | |

It is certified that error appears in the above-identified patent and that said Letters Patent is hereby corrected as shown below:

In the Specification

In Column 4, Line 58, delete "Ag/AgCl)" and insert -- AgCl) --, therefor.

Signed and Sealed this
Twenty-eighth Day of April, 2015

Michelle K. Lee
*Director of the United States Patent and Trademark Office*